(12) United States Patent
Tsuruta et al.

(10) Patent No.: US 10,016,235 B2
(45) Date of Patent: *Jul. 10, 2018

(54) ENDOSCOPE SYSTEM HAVING FIRST TRANSMISSION AND RECEPTION ELECTRODES, SECOND TRANSMISSION AND RECEPTION ELECTRODES AND ELECTRICALLY POWERED TREATMENT DEVICE POWERED TO PERFORM TREATMENT

(71) Applicant: OLYMPUS CORPORATION, Tokyo (JP)

(72) Inventors: Shoei Tsuruta, Tachikawa (JP); Yuta Sugiyama, Hachioji (JP); Akira Matsui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 395 days.

This patent is subject to a terminal disclaimer.

(21) Appl. No.: 14/841,014

(22) Filed: Aug. 31, 2015

(65) Prior Publication Data

US 2015/0366610 A1    Dec. 24, 2015

Related U.S. Application Data

(63) Continuation of application No. PCT/JP2014/050804, filed on Jan. 17, 2014.

(30) Foreign Application Priority Data

Jun. 28, 2013 (JP) .................................. 2013-136760

(51) Int. Cl.
*A61B 1/018* (2006.01)
*A61B 1/00* (2006.01)
(Continued)

(52) U.S. Cl.
CPC ...... *A61B 18/1492* (2013.01); *A61B 1/00029* (2013.01); *A61B 1/018* (2013.01);
(Continued)

(58) Field of Classification Search
CPC . A61B 1/00029; A61B 1/00027; A61B 1/018; A61B 2560/0204;
(Continued)

(56) References Cited

U.S. PATENT DOCUMENTS 5,249,585 A * 10/1993 Turner .................... A61B 5/01
600/549
5,342,381 A * 8/1994 Tidemand .......... A61B 17/2812
606/174

(Continued)

FOREIGN PATENT DOCUMENTS

CN       104321029 A     1/2015
EP       0 888 749 A1    1/1999
(Continued)

OTHER PUBLICATIONS

Extended Supplementary European Search Report dated Feb. 3, 2017 in European Patent Application No. 14 81 8805.5.
(Continued)

*Primary Examiner* — John P Leubecker
(74) *Attorney, Agent, or Firm* — Scully, Scott, Murphy & Presser, P.C.

(57) ABSTRACT

An endoscope system having: an endoscope having: a first transmission electrode arranged to a channel defined by the endoscope; and a second transmission electrode arranged to the channel, wherein the first transmission electrode and the second transmission electrode are electrically connected to the power source; and a treatment tool having: a first reception electrode arranged to a treatment tool insertion section, and spaced apart from the first transmission elec-
(Continued)

trode to form a first capacitor; a second reception electrode arranged to the treatment tool insertion section, and spaced apart from the second transmission electrode to form a second capacitor; and an electrically powered treatment device configured to be moved by the treatment tool insertion section, wherein the electrically powered treatment device is electrically connected to the first reception electrode and the second reception electrode to be powered to perform a treatment on a subject.

20 Claims, 12 Drawing Sheets

(51) Int. Cl.
| | | |
|---|---|---|
| *A61B 18/14* | (2006.01) | |
| *G02B 23/24* | (2006.01) | |
| *A61B 18/12* | (2006.01) | |
| *H02J 50/05* | (2016.01) | |
| *A61B 18/00* | (2006.01) | |
| *A61B 17/00* | (2006.01) | |

(52) U.S. Cl.
CPC ...... *A61B 18/1206* (2013.01); *A61B 18/1445* (2013.01); *G02B 23/2476* (2013.01); *H02J 50/05* (2016.02); *A61B 1/00124* (2013.01); *A61B 2017/0034* (2013.01); *A61B 2018/00178* (2013.01); *A61B 2018/00601* (2013.01); *A61B 2018/00982* (2013.01); *A61B 2018/1286* (2013.01); *A61B 2018/147* (2013.01); *A61B 2560/0214* (2013.01)

(58) Field of Classification Search
CPC .. A61B 2560/0214; A61B 2018/00178; A61B 2018/00077; A61B 2018/00982; A61B 2017/0034; H02J 50/05; H02J 50/12
See application file for complete search history.

(56) References Cited

U.S. PATENT DOCUMENTS

| | | | |
|---|---|---|---|
| 5,540,685 A * | 7/1996 | Parins | A61B 18/1442 606/48 |
| 5,817,092 A * | 10/1998 | Behl | A61B 18/1206 606/1 |
| 5,849,020 A | 12/1998 | Long et al. | |
| 5,916,215 A * | 6/1999 | Long | A61B 18/1487 606/41 |
| 6,187,002 B1 | 2/2001 | Long et al. | |
| 6,206,875 B1 | 3/2001 | Long et al. | |
| 6,949,068 B2 | 9/2005 | Taniguchi et al. | |
| 7,824,407 B2 | 11/2010 | Yamamoto et al. | |
| 9,184,595 B2 * | 11/2015 | Kurs | H01F 38/14 |
| 2004/0133189 A1 | 7/2004 | Sakurai | |
| 2005/0049633 A1 * | 3/2005 | Watanabe | A61B 10/06 606/205 |
| 2005/0182292 A1 * | 8/2005 | Suzuki | A61B 1/00133 600/104 |
| 2008/0015409 A1 * | 1/2008 | Barlow | A61B 18/1492 600/106 |
| 2010/0179384 A1 * | 7/2010 | Hoeg | A61B 1/00016 600/109 |
| 2011/0018359 A1 | 1/2011 | Wada et al. | |
| 2011/0025132 A1 * | 2/2011 | Sato | H02J 5/005 307/104 |
| 2011/0218402 A1 * | 9/2011 | Sato | A61B 1/00016 600/160 |
| 2011/0251606 A1 * | 10/2011 | Kerr | A61B 18/1402 606/34 |
| 2012/0184951 A1 * | 7/2012 | Viola | A61B 17/00234 606/34 |
| 2012/0209061 A1 | 8/2012 | Kato | |
| 2012/0221002 A1 | 8/2012 | Long et al. | |
| 2015/0057653 A1 | 2/2015 | Sugiyama | |

FOREIGN PATENT DOCUMENTS

| | | |
|---|---|---|
| EP | 1 782 742 A2 | 5/2007 |
| EP | 2 782 214 A1 | 9/2014 |
| EP | 2 865 348 A1 | 4/2015 |
| JP | S60-83633 A | 5/1985 |
| JP | 3054605 U1 | 5/1991 |
| JP | H11-99158 A | 4/1999 |
| JP | H11-128242 A | 5/1999 |
| JP | 2000-254134 A | 9/2000 |
| JP | 2002-321721 A | 11/2002 |
| JP | 2004-208922 A | 7/2004 |
| JP | 2005-224426 A | 8/2005 |
| JP | 2011-030317 A | 2/2011 |
| JP | 2012-055697 A | 3/2012 |
| JP | 2013-121201 A | 6/2013 |
| JP | 2013-123319 A | 6/2013 |
| JP | 2014-004237 A | 1/2014 |
| WO | 2013/024419 A2 | 2/2013 |
| WO | 2013/073508 A1 | 5/2013 |

OTHER PUBLICATIONS

Harakawa, Kenichi et al., "Possibility of Wireless Power Supply by Electric Coupling Technology", Takenaka Technical Research Report, No. 66, 2010, pp. 1-8, with English abstract.
International Search Report dated Aug. 6, 2013 issued in PCT/JP2013/066735.
International Search Report dated Feb. 10, 2014 issued in PCT/JP2014/050804.
Written Opinion of the International Searching Authority dated Aug. 6, 2013 issued in PCT/JP2013/066735.

* cited by examiner

ENDOSCOPE SYSTEM HAVING FIRST TRANSMISSION AND RECEPTION ELECTRODES, SECOND TRANSMISSION AND RECEPTION ELECTRODES AND ELECTRICALLY POWERED TREATMENT DEVICE POWERED TO PERFORM TREATMENT

CROSS REFERENCE TO RELATED APPLICATION

This application is a continuation of PCT International Application No. PCT/JP2014/050804, filed on Jan. 17, 2014, the entire content of which is incorporated by this reference, and claims priority to Japanese Patent Application No. JP2013-136760, filed on Jun. 28, 2013, the entire content of which is incorporated by this reference.

BACKGROUND

The present invention relates to an endoscope system for feeding power wirelessly to a device passing through a channel of a flexible endoscope.

BACKGROUND ART

U.S. Pat. No. 7,824,407 discloses high-frequency incision forceps for applying high-frequency current to a body tissue to do a treatment as a device passing through a channel of a flexible endoscope and inserted into a body.

Further, U.S. Pat. No. 6,949,068 discloses such an endoscope shape detector that passes a probe comprising multiple magnetism generating elements through a channel to detect and display the shape of an insertion section of a flexible endoscope.

A cable is connected to devices, such as the high-frequency incision forceps, the probe of the endoscope shape detector, and the like to supply power necessary for operation. However, this cable may disturb operator's operations and hence reduce operability.

U.S. Pat. No. 6,187,002 and U.S. Pat. No. 6,206,875 disclose that power is wirelessly fed from a transmission electrode of a trocar to a reception electrode of a capacitive cordless electrosurgical instrument inserted in the trocar through capacitive coupling.

It is an object of embodiments of the present invention to provide an endoscope system comprising a highly operable device inserted into a channel of a flexible endoscope.

SUMMARY

An endoscope system comprising: an endoscope comprising: an endoscope insertion section comprising a portion that is flexible, wherein the endoscope defines a channel having a distal opening in the endoscope insertion section; a first transmission electrode arranged to the channel, wherein the first transmission electrode is electrically connected to a power source configured to output a high-frequency power; and a second transmission electrode arranged to the channel, wherein the second transmission electrode is electrically connected to the power source; and a treatment tool comprising: a treatment tool insertion section configured to be movably inserted in the channel of the endoscope; a first reception electrode arranged to the treatment tool insertion section, wherein the first reception electrode is spaced apart from the first transmission electrode to form a first capacitor; a second reception electrode arranged to the treatment tool insertion section, wherein the second reception electrode is spaced apart from the second transmission electrode to form a second capacitor; and an electrically powered treatment device attached to the treatment tool insertion section to be moved by the treatment tool insertion section, wherein the electrically powered treatment device is electrically connected to the first reception electrode and the second reception electrode to be powered to perform a treatment on a subject.

DETAILED DESCRIPTION

First Embodiment

Figure 1:
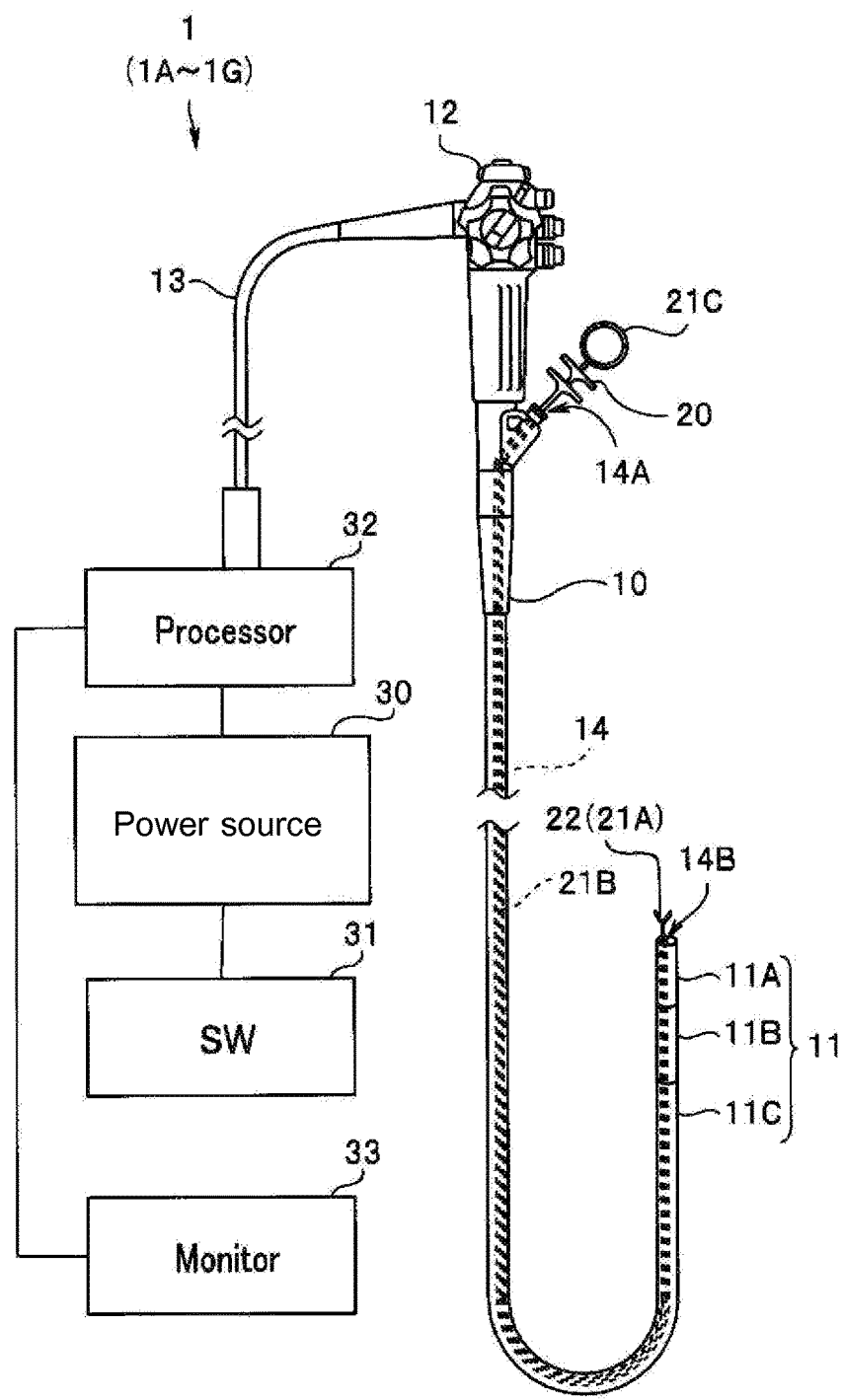
FIG. 1 is a configuration diagram of an endoscope system of a first embodiment.

As illustrated in FIG. 1, an endoscope system 1 of the embodiment comprises a flexible endoscope (hereinafter called "endoscope") 10, a treatment tool 20 as a device passing through a channel 14 of the endoscope 10, and a power source 30.

The endoscope 10 comprises an endoscope insertion section 11 and an operation section 12 arranged on a base end side of the endoscope insertion section 11, and a universal cord 13 provided to extend from the operation section 12. The endoscope insertion section 11 comprises a distal end portion 11A in which an imaging unit 15 (an image sensor such as a CCD or a CMOS) (see FIG. 2) is arranged, a curved portion 11B for changing the direction of the distal end portion 11A, and a soft portion 11C being flexible and elongated. The operation section 12 is a non-flexible section grasped by an operator to perform a directional operation of the distal end portion 11A, an air supply operation, a water supply operation, an endoscopic image taking operation, and the like. On the other hand, the endoscope insertion section 11 is a flexible section to be movably inserted from an oral cavity or an anus into an alimentary tract.

A processor 32 as a hardware connected to the universal cord 13 of the endoscope 10 comprises a control unit (not illustrated) composed of a CPU and the like for controlling the entire endoscope system 1 to process an imaging signal output from the imaging unit 15 and display an endoscopic image on a monitor 33. The power source 30 connected to the processor 32 supplies high-frequency power to the treatment tool 20. For example, a foot switch SW 31 controls ON/OFF of the output of the power source 30. Note that a line can be branched from the universal cord 13 may be connected directly to the power source 30.

The endoscope 10 comprises a flexible channel 14 made of a resin tube passing through the endoscope insertion section 11 from an insertion opening 14A of the operation section 12 to an distal opening 14B of the distal end portion 11A.

The treatment tool 20 comprises a distal end portion 21A in which a treatment unit 22 is arranged, a treatment tool insertion section 21B can be flexible and elongated, and an operation section 21C arranged on the base end side of the treatment tool insertion section 21B and operated by the operator outside the body. The treatment tool 20 is inserted from the insertion opening 14A to pass through the channel 14 and protrude the distal end portion 21A from the distal opening 14B.

The distal end portion 21A comprises a pair of blades (electrodes) 22A, 22B (see FIG. 3) as the treatment unit 22 through which high-frequency current is passed. A body tissue (affected area) LT as a treated area grasped with the pair of blades 22A, 22B (see FIG. 3) of forceps according to the operation in the operation section 21C is excised and bleeding is stopped by Joule heat generated by the high-frequency current.

The power source 30 outputs high-frequency power, for example, with a frequency of not less than 100 kHz and not more than 100 MHz. The frequency of the high-frequency power is preferably selected from frequencies allowed by the laws and the like, which is 13.56 MHz, for example. It is preferred, but not particularly limited to, that the waveform amplitude of the high-frequency power be of a sinusoidal wave.

In the endoscope system 1, the treatment tool 20 and the power source 30 are not connected by wire. However, when the treatment tool 20 is inserted into the channel 14, the treatment tool 20 receives, in wireless power transmission, power required to do a treatment from the power source 30 through the endoscope 10. Note that the wireless power transmission is the same in meaning as wireless power supply.

Figure 2:
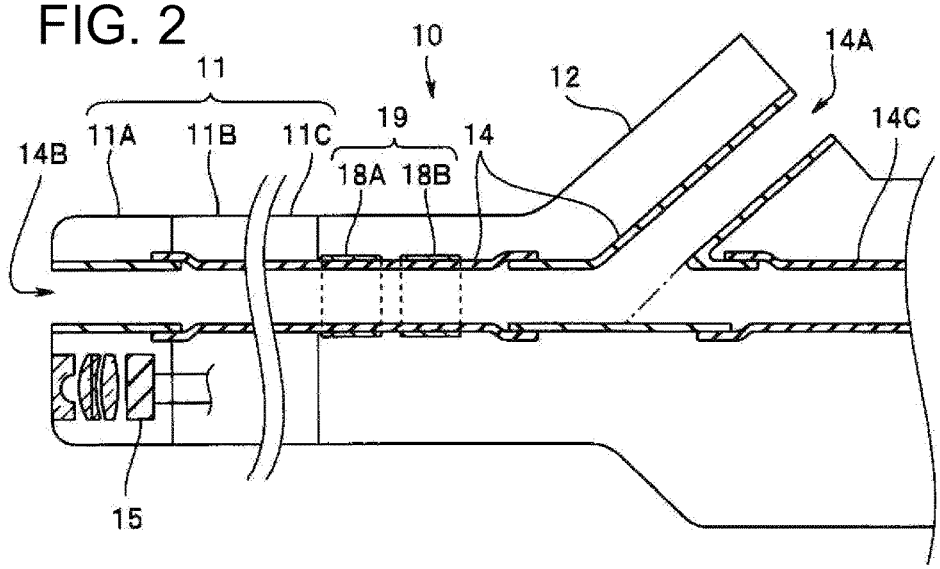
FIG. 2 is a schematic sectional view of an endoscope in the endoscope system of the first embodiment.
Figure 4:
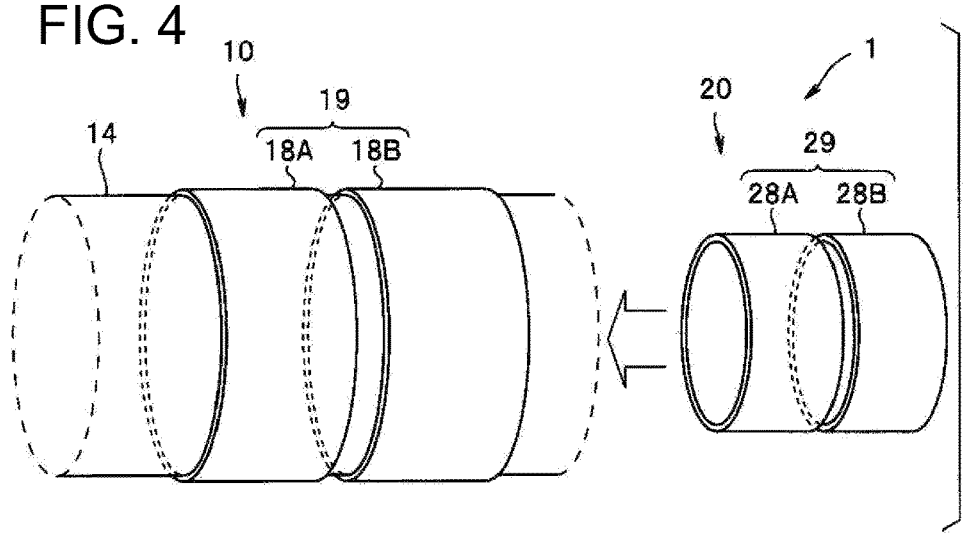
FIG. 4 is a schematic diagram of a transmission electrode and a reception electrode in the endoscope system of the first embodiment.

In other words, as illustrated in FIG. 2 and FIG. 4, the endoscope 10 comprises a power transmission unit 19 comprising a first transmission electrode 18A and a second transmission electrode 18B to convert the high-frequency power output from the power source 30 into an alternating electric field. The first transmission electrode 18A and the second transmission electrode 18B of the endoscope 10 are made of cylindrical conductors laid to cover the outer circumference of the channel 14. The first transmission electrode 18A and the second transmission electrode 18B are almost identical in diameter and length to each other (e.g., ±20%) with a gap (air gap) for insulation between both. The channel 14 comprises a flexible tube and a branch tube, and one side of the branch tube is connected to an air sending and sucking tube 14C.

The power transmission unit 19 may be structured to comprise a hollow section with which part of the channel 14 is replaced as long as it is located inside of at least either of the operation section 12 and the endoscope insertion section 11. In other words, in this specification, a component that forms the hollow section in the above structure is also regarded as part of the channel 14.

Although the conductors of the first transmission electrode 18A and the second transmission electrode 18B may be exposed to the inner surface of the hollow section in terms of the function as electrodes, it is preferred that the inner surface of the hollow section be sealed by an insulating material because the channel 14 is also used for sending and sucking air, and the like.

Figure 3:
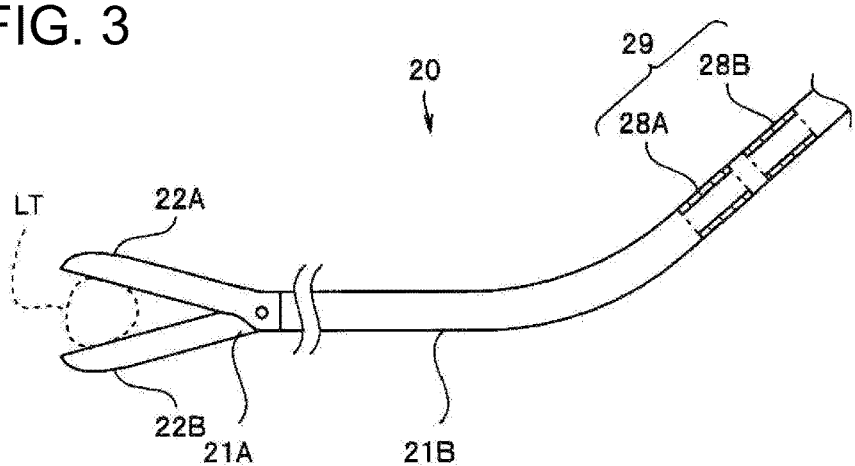
FIG. 3 is a schematic sectional view of a treatment tool in the endoscope system of the first embodiment.

On the other hand, as illustrated in FIG. 3 and FIG. 4, the treatment tool 20 comprises a power reception unit 29 comprising a first reception electrode 28A and a second reception electrode 28B to receive an alternating electric field. The first reception electrode 28A and the second reception electrode 28B of the treatment tool 20 are made up of cylindrical conductors laid along the outer circumferential surface of the insertion section 21B. The first reception electrode 28A is almost identical in diameter and length to the second reception electrode 28B with a gap (air gap) for insulation between both.

In the following description, each of the first transmission electrode 18A and the second transmission electrode 18B is called the power transmission electrode 18, and each of the first reception electrode 28A and the second reception electrode 28B is called the reception electrode 28.

Note that a region of part of the insertion section 21B, where the reception electrode 28 is arranged, is so arranged that the conductor will not be exposed to the outermost circumferential surface, and if it can be inserted into the channel 14, the outer diameter φ (20) of the region may be made larger than other regions.

Figure 5A:
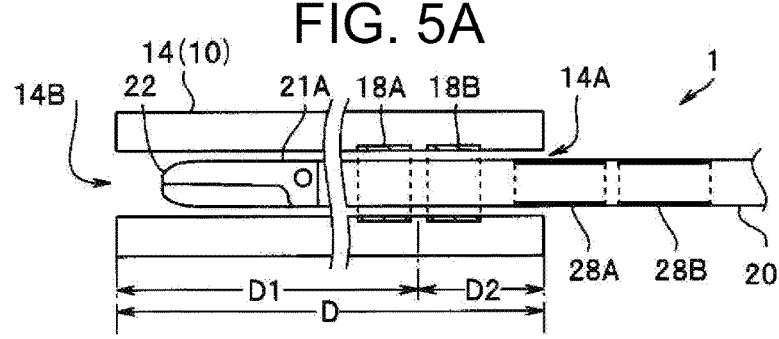
FIG. 5A is a schematic sectional view of the endoscope system of the first embodiment.

Here, as illustrated in FIG. 5A, even when the treatment tool 20 is inserted into the channel 14 from the insertion opening 14A, the reception electrode 28 of the treatment tool 20 cannot efficiently receive an alternating electric field generated by the power transmission electrode 18 of the endoscope 10 until the treatment unit 22 protrudes from the distal opening 14B.

Figure 5B:
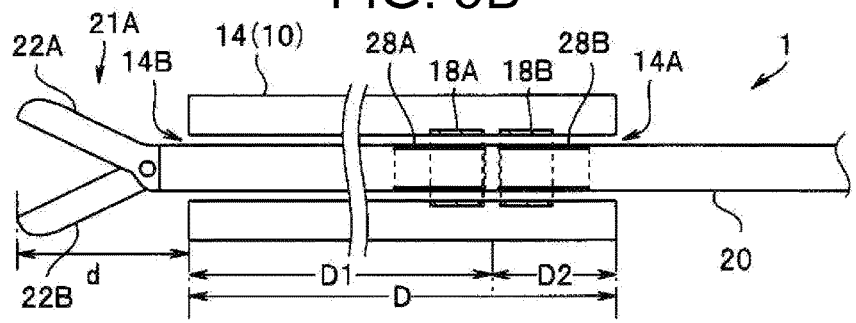
FIG. 5B is a schematic sectional view of the endoscope system of the first embodiment.

On the other hand, in a state where the treatment unit 22 is protruding from the distal opening 14B as illustrated in FIG. 5B, i.e., in a state where the treatment tool 20 is inserted in the channel 14 so that the treatment unit 22 will operate, the reception electrodes 28A and 28B are in a state of being inserted in the transmission electrodes 18A and 18B, respectively. Therefore, in the endoscope system 1, the reception electrode 28 and the power transmission electrode 18 are strongly capacitively coupled to each other in the state where the treatment unit 22 is protruding from the distal opening 14B so that the alternating electric field generated by the power transmission electrode 18 can be received efficiently.

The transmission electrodes 18A and 18B laid along the outer surface of the cylindrical channel, and the reception electrodes 28A and 28B laid along the outer surface of the cylindrical treatment tool are both cylindrical.

Figure 6A:
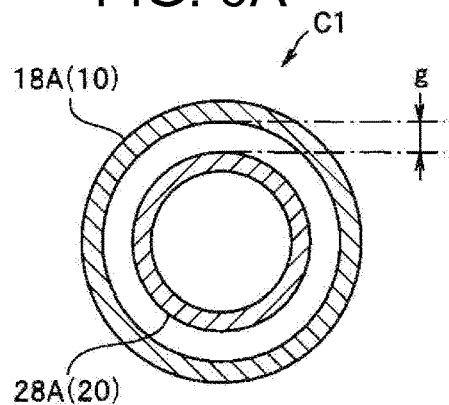
FIG. 6A is a sectional view of the transmission electrode and the reception electrode in the endoscope system of the first embodiment.
Figure 6B:
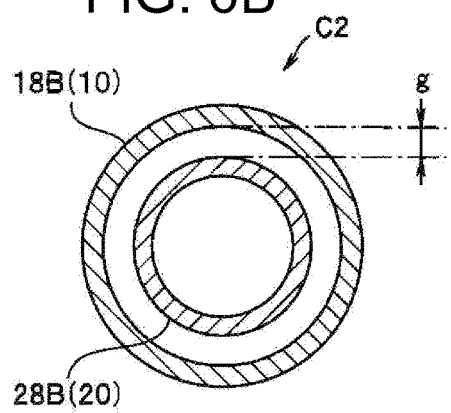
FIG. 6B is a sectional view of the transmission electrode and the reception electrode in the endoscope system of the first embodiment.

Therefore, in a state where the first reception electrode 28A is inserted in the first transmission electrode 18A as illustrated in FIG. 6A, the first transmission electrode 18A and the first reception electrode 28A arranged opposite to each other in a concentric fashion form a first capacitor C1. On the other hand, as illustrated in FIG. 6B, the second transmission electrode 18B and the second reception electrode 28B arranged opposite to each other in a concentric fashion form a second capacitor C2 in the same manner.

In the endoscope system 1, the treatment tool 20 has no physical contact (connection) with the endoscope 10 through the conductor. However, the power reception unit 29 of the treatment tool 20 is capacitively coupled to the power transmission unit 19 of the endoscope 10.

Figure 7:
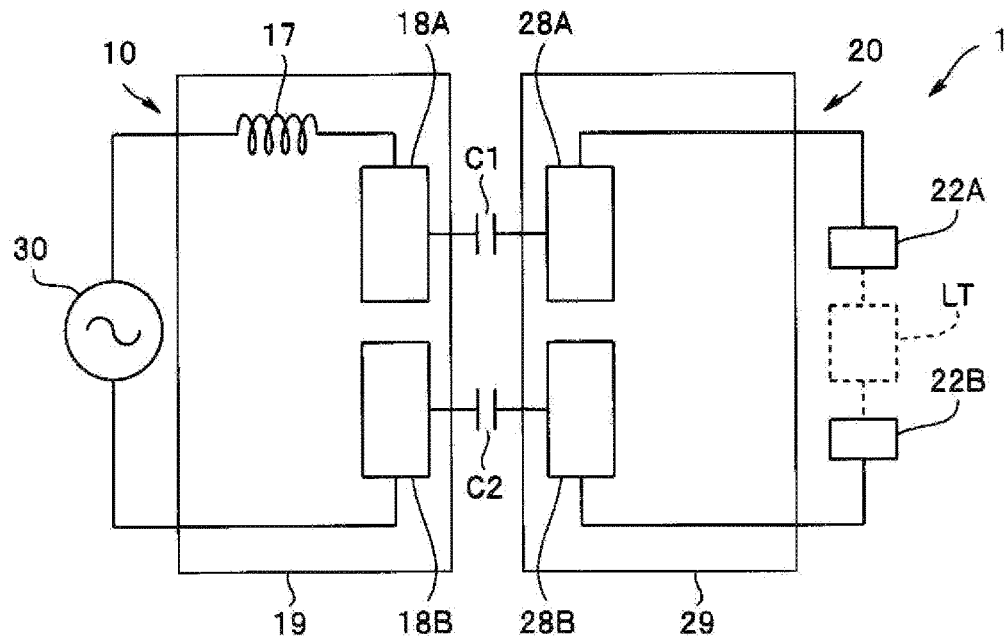
FIG. 7 is an equivalent circuit diagram of the endoscope system of the first embodiment.

As a result, as illustrated in FIG. 7, the high-frequency power output from the power source 30 of the endoscope 10 in the endoscope system 1 is output to the treatment unit 22 of the treatment tool 20 through the capacitors C1 and C2. Note that wiring for connection between the power source 30 and the second transmission electrode 18B may be ground connection.

The power from the power transmission unit 19 is transmitted to the power reception unit 29 capacitively coupled to supply power to the treatment tool 20.

Here, the efficiency of wireless transmission through capacitive coupling is proportional to the magnitude of capacitive coupling between the power transmission electrode 18 and the reception electrode 28, i.e. the capacitances CA and CB of the capacitors C1 and C2 formed by the power transmission electrode 18 and the reception electrode 28.

Note that the capacitance CA of the capacitor C1 and the capacitance CB of the capacitor C2 are substantially the same.

The capacitance C of the capacitor is proportional to a dielectric constant $\in$ between electrodes and a counter electrode area A, and inversely proportional to an inter-electrode distance g.

In other words, $C=\in A/g$.

As illustrated in FIG. 6A and FIG. 6B, the inner diameter φ (14) of the channel 14 is larger than the outer diameter φ (20) of the treatment tool insertion section 21B so that the treatment tool insertion section 21B of the treatment tool 20 can be inserted. For example, φ (14)=2.8 mm and φ (20)=2.6 mm. Assuming that the thickness of the channel 14 is regarded as zero, when the electrodes of the capacitors C1 and C2 are coaxial with each other and not eccentric, the inter-electrode distance g therebetween is very short as 0.1 mm. Further, the counter electrode area A is proportional to a length L of a shorter electrode.

Therefore, it is preferred that the length of the power transmission electrode 18 and the reception electrode 28 be 1 cm or more. If the length is in the above range or more, power can be transmitted and received. On the other hand, the maximum length of the power transmission electrode 18 and the reception electrode 28 is determined by a length D of the channel 14. For example, the channel length D of the flexible endoscope 10 is about not less than 100 cm and not more than 230 cm. There is the gap (air gap) of a predetermined length a between the first transmission electrode 18A and the second transmission electrode 18B. Therefore, the maximum length of the first transmission electrode 18A and the second transmission electrode 18B is about (D−α)/2. The maximum length of the reception electrode 28 is also about (D−α)/2.

Note that it is particularly preferred that the length of the power transmission electrode 18 and the reception electrode 28 be not less than 5 cm and not more than 100 cm in terms of the transmission/reception efficiency and the self-inductance.

Note that an insulating material comprising a high dielectric constant $\in$, such as fluorocarbon resin, may be arranged between the power transmission electrode 18 and the reception electrode 28 to increase the capacitance C.

The capacitance C may be increased by a mechanism for making the center positions of the power transmission electrode 18 and the reception electrode 28 eccentric to each other, or a mechanism for pressing the channel with the power transmission electrode 18 laid to deform to the center side or to one side in order to reduce the inter-electrode distance g locally.

A state in which the capacitance becomes the highest with the capacitors made not eccentric is a state in which the reception electrode 28 is inserted into the entire length of the power transmission electrode 18. Therefore, it is preferred that the length of the reception electrode 28 be longer than the length of the power transmission electrode 18, and in light of the protrusion amount d from the distal opening 14B of the treatment tool 20, it is particularly preferred that the total length of the two reception electrodes 28 be (total length of the two transmission electrodes 18+gap α+protrusion amount d). Note that the protrusion amount d is, for example, not less than 1 cm and not more than 10 cm, though it depends on the treatment tool.

The minimum length of the power transmission electrode 18 and the like is a length at which parasitic capacitance in the circuit and capacitance involved in transmitting/receiving power, i.e. combined capacitance of the capacitance CA of the capacitor C1 and the capacitance CB of the capacitor C2 becomes substantially the same as each other. When the parasitic capacitance in the circuit is higher than the capacitance involved in transmitting/receiving power, most of the supplied power does not reach the treatment unit.

Further, when the treatment unit consumes more of the power input from the power transmission unit to the power reception unit, transmission efficiency becomes higher. Therefore, it is preferred that the load on the treatment unit, i.e., the resistance should be large compared with various resistive components in the circuit.

In other words, although the example in which the power transmission electrode 18 is arranged in the operation section 12 of the channel 14 is illustrated in FIG. 2, it may be arranged in the soft portion 11C of the channel 14, or arranged in the operation section 12 and the soft portion 11C of the channel 14. Further, the first transmission electrode 18A may be arranged in the operation section 12 of the channel 14 and the second transmission electrode 18B may be arranged in the soft portion 11C of the channel 14.

Further, although the length of the reception electrode 28 illustrated in FIG. 3 is short, it may be, for example, an electrode having almost the same length as the length of the insertion section 21B.

The power transmission electrode 18 and the reception electrode 28 are only need to be arranged in positions where the electrodes are strongly capacitively coupled to each other when the treatment unit is in operation. Note that the power transmission electrode 18 and the reception electrode 28 placed inside the flexible, soft portion 11C need to be flexible.

In the endoscope system 1, the channel 14 is so used that capacitors C1 and C2 short in inter-electrode distance g, wide in counter electrode area A, and high in capacitance C can be formed.

Although the length D of the channel 14 of the endoscope 10 is very long as 100 cm or more, most of the length is placed inside the flexible, soft portion 11C. The endoscope system 1 comprising the flexible endoscope 10 comprising the flexible, elongated endoscope insertion section 11 (channel 14) is high in the efficiency of wireless power transmission because it can increase the length of the power transmission electrode 18 and the reception electrode 28 according to the length of the endoscope insertion section 11.

Although it is easy to set the length of the power transmission electrode 18 and the reception electrode 28 to 5 cm or more, the power transmission electrode 18 and the reception electrode 28 placed inside the flexible, soft portion 11C need to be flexible.

Further, since the capacitors C1 and C2 are made up of concentric counter electrodes, even when the treatment tool 20 rotates in the channel 14 around the longitudinal direction as its axis, the power transmission electrode 18 and the reception electrode 28 are capacitively coupled stably. Thus, the operator can carry out an insertion operation without being conscious of the rotation of the treatment tool 20.

As already described, the power transmission electrode 18 is made of cylindrical metal laid to cover the outer circumference of the channel 14. For example, a metal film made of copper or the like is formed on the outer circumferential surface of the channel 14 as a flexible tube by an evaporation method or a plating method to enable the formation of the power transmission electrode 18.

The reception electrode 28 can also be made by forming a metal film on the outer circumferential surface of the treatment tool insertion section 21B of the treatment tool 20 in the same manner as the power transmission electrode 18. Note that it is preferred that the surfaces of the power transmission electrode 18 and the reception electrode 28 should be covered with insulating films to ensure the insulating performance and reliability.

The power transmission electrode 18 and the reception electrode 28 made of the metal films are easy to be laid on curved surfaces, and have flexibility.

Here, it is preferred that the same treatment tool 20 can be used even for multiple endoscopes different in channel length D. To this end, it is preferred that the arrangement position of the power transmission electrode 18 should be set with reference to the distal opening 14B. In other words, the center of gravity of the power transmission electrode 18 of the endoscope only needs to be arranged in a position a predetermined distance D1 from the distal opening 14B. Here, the center of gravity means a center position in the longitudinal direction of the entire length of an electrode involved in transmitting or receiving power. When the electrode is divided into multiple parts in the longitudinal direction, it is a center position of the entire length comprising all the parts. In this case, distance D2 from the insertion opening 14A to the power transmission electrode 18 in an endoscope comprising a longer channel length D becomes longer than that of an endoscope having a shorter channel length D.

In an endoscope system comprising multiple endoscopes, in each of which the power transmission electrode 18 is arranged in a position a predetermined distance D1 from the distal opening 14B, respectively, and the treatment tool 20, the multiple endoscopes can wirelessly feed power to the treatment tool 20 efficiently.

It goes without saying that an endoscope system comprising one endoscope and multiple treatment tools has the same effect, where the power reception unit 29 is arranged in a position capable of receiving the alternating electric field generated by the power transmission unit 19 most efficiently in a state of inserting each of the treatment tools into the channel 14 up to the operating position, respectively.

In an endoscope system 1, as illustrated in an equivalent circuit diagram of FIG. 7, an endoscope side circuit comprising a power source 30 and a power transmission unit 19 has no physical contact through a conductor with a treatment tool side circuit comprising a power reception unit 29 and treatment units 22 (22A, 22B) to apply current to a body tissue LT as a load section that consumes power.

However, the power reception unit 29 is capacitively coupled to a non-radiative alternating electric field generated in a space near the power transmission unit 19. The power is supplied to the treatment unit 22 of the treatment tool 20 through the power reception unit 29 capacitively coupled.

Since the treatment tool 20 in the endoscope system 1 has no wiring (cable) connected to the power source 30, it is easy to handle the treatment tool 20 with good operability. Further, since the power transmission unit 19 is arranged inside the endoscope 10, a generated electromagnetic field is less likely to leak outside the endoscope 10, and the influence of the leakage electromagnetic field on peripheral devices is small. Further, since distance between a living body as an object to be treated and the power transmitting/receiving units is ensured, the influence of heat generation is small.

Further, since the cylindrical reception electrode 28 is coaxial with the cylindrical power transmission electrode 18 and the counter electrode area is largest among same-sized counter electrodes, the capacitance C of the capacitor is high. In addition, the reception electrode 28 and the transmission electrode 18 can be arranged over the entire length of the endoscope insertion section 11 of the flexible endoscope 10, it is easy to further increase the capacitance.

Further, since a relative positional relationship between the power transmission unit 19 and the power reception unit 29 is defined by arranging the power transmission unit 19 inside the endoscope 10, the state of strongly capacitive coupling between the power transmission unit 19 and the power reception unit 29, i.e., a state of high power transmission efficiency can be maintained stably, and energy saving performance is excellent as well.

Further, as illustrated in FIG. 7, the endoscope system 1 may comprise an inductance element 17 in a power transmission/reception circuit comprising the power transmission unit 19 of the endoscope 10 and the power reception unit 29 of the treatment tool 20. The addition of an inductance component causes the power transmission/reception circuit to form a serial resonance circuit with a predetermined resonant frequency F1.

Then, circuit capacitance Ctotal comprising the capacitance CA of the capacitor C1 and the capacitance CB of the capacitor C2, circuit inductance Ltotal comprising the inductance element 17, and a frequency F0 of high-frequency power output from the power source 30 have the following relation (Equation 1).

$$\sqrt{L_{total} \cdot C_{total}} = 1/2\pi F1 = 1/2\pi F0 \qquad (\text{Eq. 1})$$

In other words, the frequency F0 of the high-frequency power output from the power source 30 coincides with the resonant frequency F1 of the power transmission/reception circuit. Therefore, the high-frequency power output from the power source 30 is efficiently output to the treatment unit 22.

Instead of the inductance element 17, the power reception unit 29 of the treatment tool 20 may comprise an inductance element, or the power transmission unit 19 and the power reception unit 29 may comprise inductance elements, respectively.

Here, voltage across the terminals of the inductance element in the resonance circuit is the same as the voltage across the terminals of the capacitor, and the inductance of the inductance element is set to compensate for a reactance using the capacitance of the capacitor and a specific frequency. Here, when only the voltage across the terminals of a more essential capacitor is discussed, the voltage across the terminals is inversely proportional to the capacitance. Therefore, the higher the capacitance of the capacitor, the lower the voltage across the terminals, and this can lead to reducing risk of insulation breakdown. However, when the capacitance is too high, self-resonance may occur due to the self-inductance of the resonance circuit even without any inductance element 17, and this can deteriorate controllability. The capacitance needs to be low to arrange an inductance element in order to improve controllability. Thus, the capacitance is set in consideration of trade-off between the risk of insulation breakdown and controllability. Since the voltage across the terminals of the inductance element is proportional to the inductance, though not described in detail, the inductance element acts in an opposite way to the capacitance element.

Here, in the endoscope system 1, a switch is used to control ON/OFF of the power output to the treatment tool 20 as already described above. The switch is illustrated as the foot switch 31 in FIG. 1, but the switch may be arranged in the power source 30, the operation section 12 of the endoscope 10, or the operation section 21C of the treatment tool 20.

The switch connected to the power source 30 or the switch arranged in the power source 30 controls ON/OFF of the output of the power source 30. The switch arranged in the operation section 12 or the operation section 21C controls ON/OFF of power through an internal circuit of the power transmission unit 19 or the power reception unit 29. Instead of the ON/OFF control in the power transmission/reception circuit, a Q value of the power transmission/reception circuit can be increased/decreased to make a vast change in transmission/reception efficiency in order to obtain the same effect as the ON/OFF control. However, when the amount of power is large, the control of decreasing the Q value may cause a problem such as heat generation.

Note that the switch may be a button switch, a touch gesture-capable operating part, a speech-recognition operating part, or the like.

As described above, in the endoscope system 1, the switch as power transmission starting/stopping means for starting or stopping output from the power source 30 is arranged separately from the power source 30, or arranged in the operation section 12 of the endoscope 10 or in the treatment tool 20.

Variations of First Embodiment

Next, endoscope systems 1A to 1F, and the like as variations 1 to 6 of the first embodiment will be described. Since the endoscope systems 1A to 1F, and the like comprise the same components as the endoscope system 1 already described and are similar to the endoscope system 1, the same reference numerals are given to components having the same functions to omit the description thereof.

All the endoscope systems 1A to 1F, and the like have the effects of the endoscope system 1, and further have more beneficial effects than the endoscope system 1, respectively.

<Variation 1> Resonance Control

Figure 8:
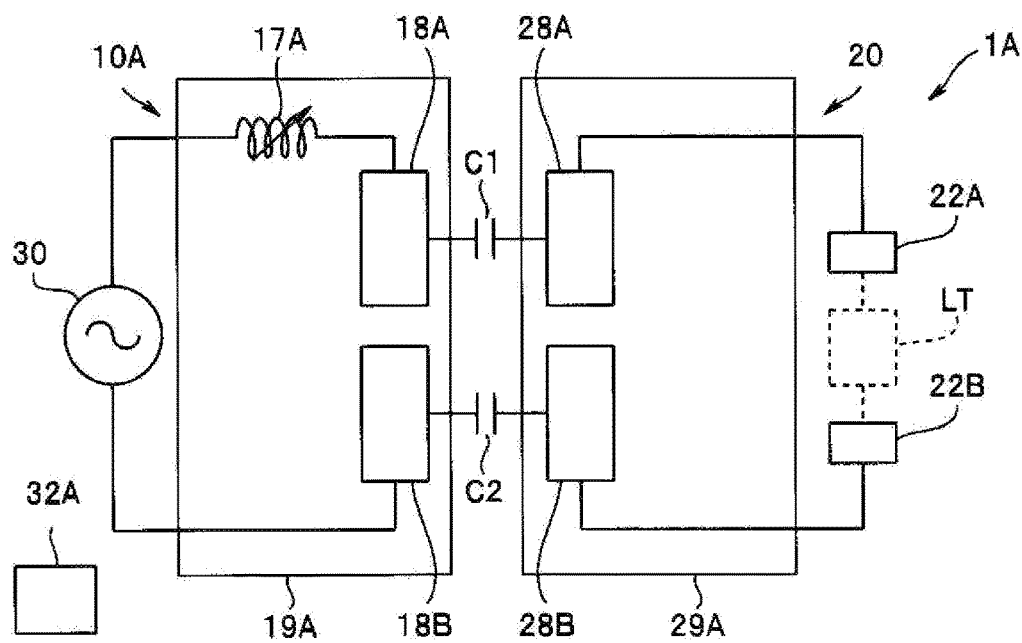
FIG. 8 is an equivalent circuit diagram of an endoscope system as a variation 1 of the first embodiment.

In the endoscope system 1A, as illustrated in FIG. 8, an inductance element 17A is a variable inductance element. Then, a control unit 32A adjusts the inductance of the inductance element 17A to make the resonant frequency F1 of the resonance circuit coincide with the frequency F0 of high-frequency power output from the power source 30. The control unit 32A is, for example, arranged in the processor 32, the power source 30, or the endoscope 10.

When the positional relationship between the power transmission electrode 18 and the reception electrode 28, the treatment condition, or the like is changed, the resonant frequency F1 of the resonance circuit varies. However, in the endoscope system 1A, the resonant frequency F1 is adjusted to coincide with the frequency F0 of high-frequency power.

Therefore, power input from the power source 30 to the resonance circuit is highly efficient.

Note that the control unit 32A may control the power source 30 according to the change in the resonant frequency F1 of the power transmission/reception circuit to change the frequency F0 of high-frequency power or an output value of the high-frequency power.

In the above description, the inductance element 17A is described as part of the power transmission unit 19A, but the inductance element 17A and the control unit 32A may be, for example, part of the processor 32. Further, the inductance element 17A and the like may be arranged in the operation section 21C of the treatment tool 20. In other words, the inductance element 17A and the control unit 32A have only to be comprised in any of the components in the endoscope system 1A.

When a power supply with a nonzero output impedance, for example, a 50Ω power supply is used as the power source 30, an impedance matching circuit may be arranged before the power transmission unit to make the impedance on the treatment unit side of the power transmission unit coincide with the output impedance of the power supply in order to suppress reflection so that the efficiency of power input from the power source 30 to the resonance circuit will be increased.

The impedance matching circuit composed of a combination of two or more elements such as a capacitance element and an inductance element may be part of the processor 32, or may be arranged in the operation section 21C of the treatment tool 20.

<Variation 2> Electrode Structure

The distribution of a generated alternating electric field, a capacitive coupling state, and the like greatly vary depending on the electrode structure and arrangement of the power transmitting/receiving units. However, power can be wirelessly transmitted as long as the structure is such that an alternating electric field generated in the power transmission unit 19 causes capacitive coupling to the power reception unit 29.

In the endoscope system 1, although the description is made by taking the cylindrical metal films as an example of the power transmission electrode 18 of the power transmission unit 19 and the reception electrode 28 of the power reception unit 29, the electrodes for generation of an alternating electric field and power reception are not limited to the cylindrical metal films. FIG. 9A to FIG. 12 illustrate electrodes as variations of the power transmission electrode 18 and the reception electrode 28.

Note that the structure of the reception electrode 28 of the power reception unit 29 may be the same as or different from the power transmission electrode 18 of the power transmission unit 19.

Figure 9A:
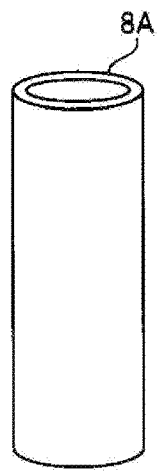
FIG. 9A is a schematic diagram of an electrode as a variation 2 of the endoscope system of the first embodiment.
Figure 9B:
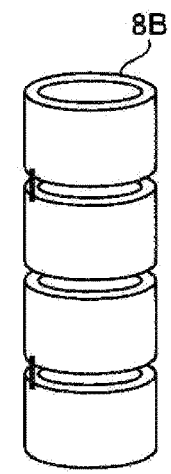
FIG. 9B is a schematic diagram of an electrode as the variation 2 of the endoscope system of the first embodiment.
Figure 9C:
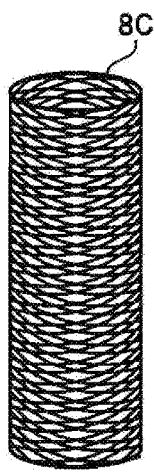
FIG. 9C is a schematic diagram of an electrode as the variation 2 of the endoscope system of the first embodiment.
Figure 9D:
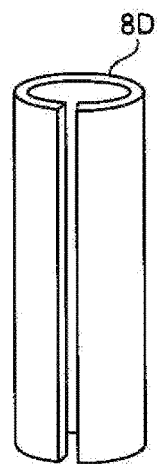
FIG. 9D is a schematic diagram of an electrode as the variation 2 of the endoscope system of the first embodiment.
Figure 9E:
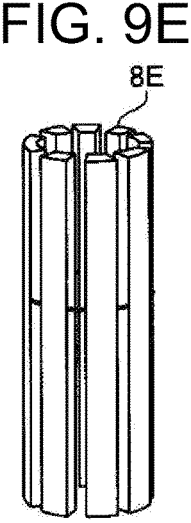
FIG. 9E is a schematic diagram of an electrode as the variation 2 of the endoscope system of the first embodiment.

An electrode 8A in FIG. 9A is made of a metal member, made by shaping copper foil or the like into a cylinder, or of a copper tube or the like. An electrode 8B in FIG. 9B is made by coupling multiple cylindrical metal members and electrically connecting the metal members. The electrode 8B will have flexibility even if each of the cylindrical metal members has low flexibility. Since an electrode 8C in FIG. 9C is made of a metal member formed into a mesh, it has flexibility. Since an electrode 8D in FIG. 9D comprises a slit formed in the longitudinal direction, a reduction in eddy current loss is small. An electrode 8E in FIG. 9E is divided by multiple slits, but respective pieces are electrically connected. Since the electrode 8E is divided into multiple elongated members, it has flexibility.

Figure 9F:
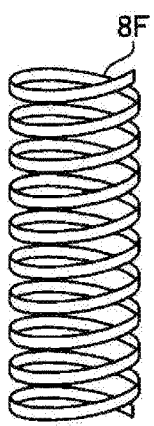
FIG. 9F is a schematic diagram of an electrode as the variation 2 of the endoscope system of the first embodiment.
Figure 9G:
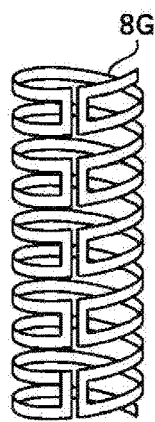
FIG. 9G is a schematic diagram of an electrode as the variation 2 of the endoscope system of the first embodiment.
Figure 9H:
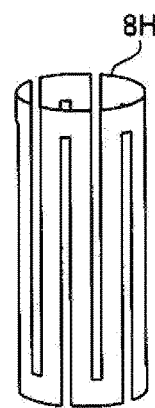
FIG. 9H is a schematic diagram of an electrode as the variation 2 of the endoscope system of the first embodiment.

An electrode 8F in FIG. 9F comprises a spiral form. Although adjacent element wires are in non-contact with each other in the electrode 8F, it is preferred that the electrode 8F be a so-called densely wound coil with adjacent element wires being in contact and conductive with each other to reduce self-inductance. An electrode 8G in FIG. 9G is formed into a spiral shape comprising folded portions. An electrode 8H in FIG. 9H comprises folded portions at the edges in the longitudinal direction.

Here, a densely wound spiral coil may be arranged in the treatment tool insertion section 21B of the treatment tool 20 to ensure flexibility and mechanical strength. In this case, the reception electrode 28 can be formed by using part of a shape holding spiral coil of the treatment tool 20, which comprises the same structure as the electrode 10F, to reduce the size and cost of the treatment tool 20.

In other words, a conducting wire for energization is connected to the shape holding spiral coil so that it can be used as the reception electrode 28. When the shape holding spiral coil is made of stainless steel or the like comprising a relatively high electric resistance, it is preferred that a low-resistance metal material should be formed on the surface by plating with copper, silver, or the like to reduce the electric resistance. Alternatively, at least part of the stainless coil may be replaced by a coil made of a low-resistance metal material so that it will be used as the reception electrode 28.

Figure 9I:
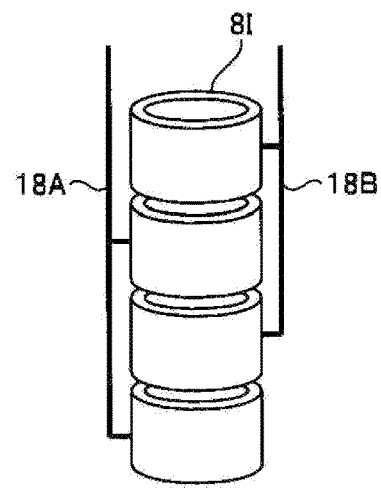
FIG. 9I is a schematic diagram of an electrode as the variation 2 of the endoscope system of the first embodiment.

Although an electrode 8I illustrated in FIG. 9I is similar in structure to the electrode 8B, each of adjacent cylindrical metal members is used as the transmission electrode 18A or the transmission electrode 18B, respectively. In other words, the adjacent cylindrical metal members are not connected. In the electrode 8I, the capacitance CA of capacitor C1 and the capacitance CB of the capacitor C1 will be little different from each other even if the flexible channel 14 is highly deformed to change each inter-electrode distance gA between the transmission electrode 18A and the reception electrode 28A, and each inter-electrode distance gB between the transmission electrode 18B and the reception electrode 28B. In other words, the change in capacitance CA of the capacitor C1 and the change in the capacitance CB of the capacitor C2 are averaged. Thus, even if the channel 14 is highly deformed, the transmission/reception efficiency is less likely to change drastically.

Figure 10:
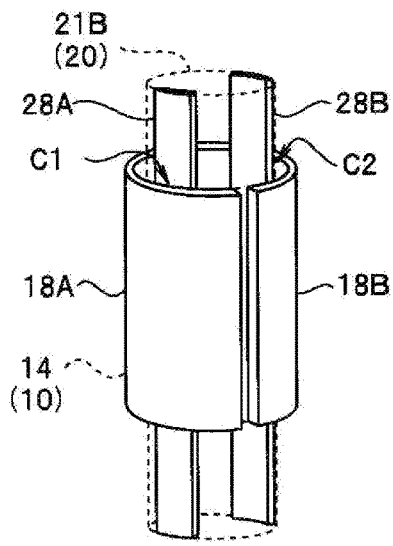
FIG. 10 is a schematic diagram of electrodes as the variation 2 of the endoscope system of the first embodiment.
Figure 11:
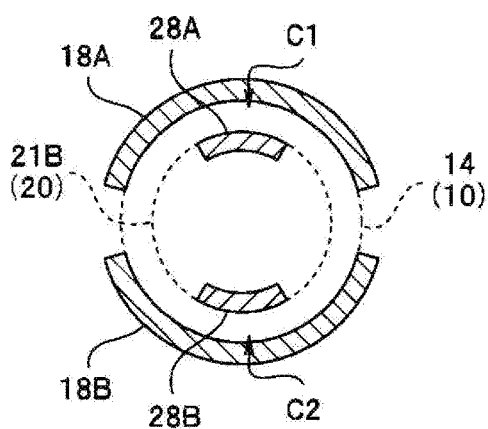
FIG. 11 is a schematic sectional view of the electrodes as the variation 2 of the endoscope system of the first embodiment.

Further, as illustrated in FIG. 10 and FIG. 11, the power transmission electrode 18 and the reception electrode 28 may be placed to form two pairs of capacitors C1 and C2 at the same position in the longitudinal direction. Compared with a case where the power transmission electrode 18 and the reception electrode 28 are arranged in the longitudinal direction, since this structure allows respective electrode lengths to be reduced to half or the maximum length of the electrode lengths to be doubled, the design freedom is high.

Figure 12:
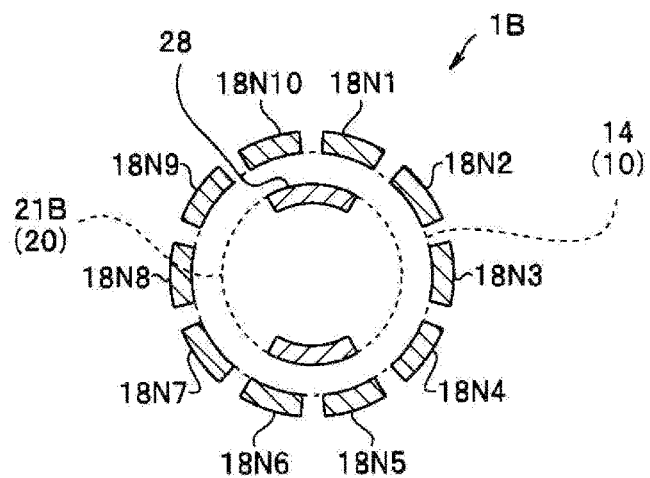
FIG. 12 is a schematic sectional view of the electrodes as the variation 2 of the endoscope system of the first embodiment.

In an endoscope system 1B illustrated in FIG. 12, the power transmission electrode 18 is divided into ten parts, i.e., transmission electrodes 18N1 to 18N10. The transmission electrodes 18N1 to 18N10 are connected to the power source 30 through respective switching elements (not illustrated). The treatment tool 20 is rotatable inside the channel 14.

In the endoscope system 1B, some of the transmission electrodes 18N1 to 18N10 are selected as being capacitively coupled most strongly to the reception electrodes 28 to form the capacitors C1 and C2. It is preferred that the number of electrode divisions be not less than three and not more than ten. A predetermined effect can be obtained within the above range.

In the endoscope system 1B, even if the electrode is divided, a change in power transmission efficiency with respect to the rotation of the treatment tool 20 around the longitudinal direction as the axial center can be suppressed.

<Variation 3> Resonance Structure

Figure 13:
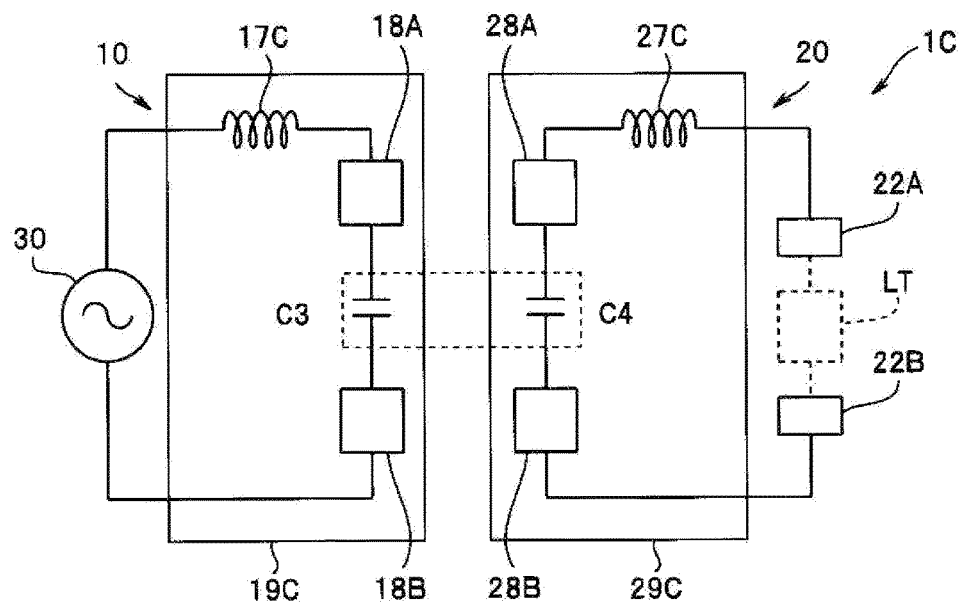
FIG. 13 is an equivalent circuit diagram of an endoscope system as a variation 3 of the first embodiment.

In an endoscope system 1C, as illustrated in FIG. 13, the transmission electrodes 18A and 18B form a capacitor C3 that generates an alternating electric field as a near field. Then, the reception electrodes 28A and 28B form a capacitor C4, and the capacitor C4 is capacitively coupled to the alternating electric field generated by the capacitor C3.

Figure 14A:
FIG. 14A is a schematic diagram of electrodes in an endoscope system as a variation 3 of the first embodiment.
Figure 14B:
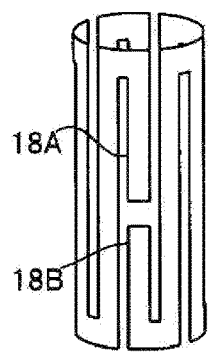
FIG. 14B is a schematic diagram of electrodes in the endoscope system as the variation 3 of the first embodiment.
Figure 14C:
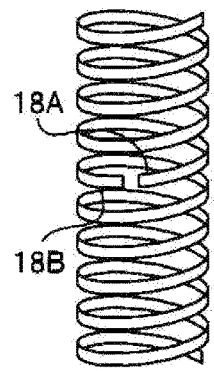
FIG. 14C is a schematic diagram of electrodes in the endoscope system as the variation 3 of the first embodiment.
Figure 14D:
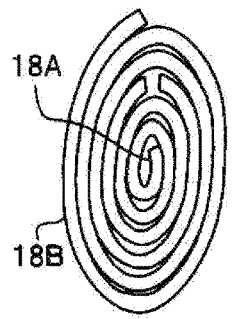
FIG. 14D is a schematic diagram of electrodes in the endoscope system as the variation 3 of the first embodiment.

For example, as illustrated in FIG. 14A, the transmission electrode 18A and the transmission electrode 18B (reception electrode 28A and the transmission electrode 18B) are arranged in the form of a dipole antenna.

Further, in the endoscope system 1C, a power transmission unit 19C and a power reception unit 29C comprise inductance elements 17C and 27C, respectively, to form an independent resonance circuit. Then, a resonant frequency F1C of the power transmission unit 19C and a resonant frequency F2C of the power reception unit are the same as the frequency F0 of the high-frequency power.

Figure 14E:
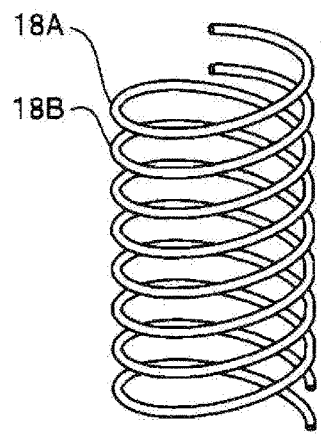
FIG. 14E is a schematic diagram of electrodes in the endoscope system as the variation 3 of the first embodiment.

Note that the power transmission electrode 18 and the reception electrode 28 may be formed as illustrated in any of FIG. 14B to FIG. 14E. FIG. 14B to FIG. 14E illustrate structures in which dipole antenna-shaped electrodes illustrated in FIG. 14A are folded or wound. FIG. 14E illustrates a structure in which two electrodes paired in the longitudinal direction are wound in the shape of a double helix. Since the electrodes wound in the shape of the double helix can obtain higher capacitance than those folded or wound in the opposite directions, the transmission efficiency is high. Further, since the electric field is distributed in a wide range in the longitudinal direction, the positional degree of freedom of the treatment tool 20 is high and operability is excellent.

<Variation 4> Shielding Member

Figure 15:
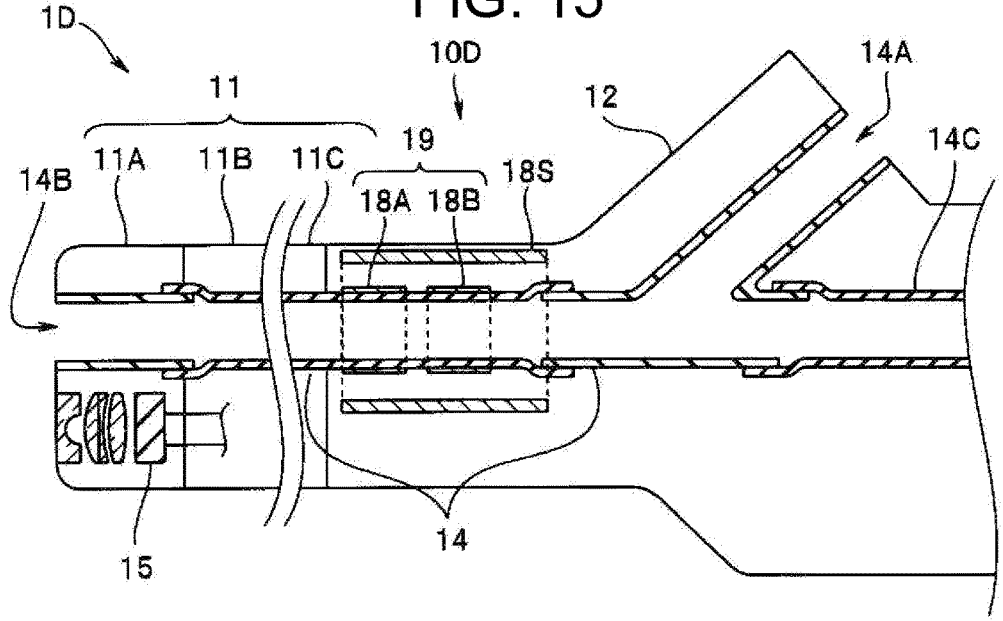
FIG. 15 is a schematic sectional view of an endoscope in an endoscope system as a variation 4 of the first embodiment.

In the endoscope system 1, since the power transmission unit 19 is arranged inside the endoscope 10 as already described, a generated electromagnetic field is less likely to leak outside the endoscope 10. In order to prevent a further leakage electromagnetic field, an endoscope system 1D comprising an endoscope 10D with a shielding member 18S arranged therein to shield an electromagnetic field as illustrated in FIG. 15 is preferable. Although the shielding member 18S only needs to be arranged to cover at least part of the outer circumference of the power transmission electrode 18, it is preferred that shielding member 18S should be arranged to cover the outer circumference completely.

As the shielding member 18S, a conductive material, for example, a metal material such as gold, silver, copper, aluminum, or stainless steel, highly doped semiconductor, conductive resin, or the like is used. Note that use of a soft magnetic material such as Permalloy as the shielding member allows the shielding member to obtain not only the shielding effect, but also an effect as a magnetic yoke for controlling the path of magnetic lines. Here, the shielding member 18S may be connected to the ground (ground-connected).

As described above, the channel 14 is covered with the shielding member 18S covering the power transmission unit 19 in the endoscope system 1D.

<Variation 5> Treatment Tool

As devices in the endoscope system 1, various bipolar treatment tools, each comprising a load section operating with power received by the power reception unit 29, can be used. In other word, for example, high-frequency incision forceps, high-frequency hemostatic forceps, hot biopsy forceps, a high-frequency coagulation treatment tool, an AC generating treatment tool for plasma, a heating treatment tool, a cooling treatment tool, a vibrating treatment tool, a radiation treatment tool, or the like can be used as the treatment tool 20.

Further, the devices are not limited to treatment tools for applying high-frequency power to the body tissue LT to do treatments, and the devices may also be various electric-driven treatment tools. For example, the endoscope system can be used for an ultrasonic treatment tool using ultrasonic vibration to make an incision in a body tissue and coagulate the body tissue, an ultrasonic suction treatment tool using ultrasonic vibration to grind and suck a body tissue, a resection treatment tool using a turning force of a drill or the like to grind a body tissue, a treatment tool with an actuator having the function of electrically driving the tips of forceps, and the like.

Further, even a device such as a probe, which is passed through the channel 14 but the distal end portion 21A thereof does not protrude from the distal opening 14B, can output wirelessly transmitted power to the load section in the same manner as the treatment tool 20. In other words, the devices in the present invention comprise a probe and the like that are passed through the channel 14 but the distal end portion 21A thereof does not protrude from the distal opening 14B.

For example, even a probe comprising multiple magnetism generating elements of an endoscope shape detector for detecting an endoscope insertion shape is a device of the present invention. Power received through wireless transmission is output to the magnetism generating elements as a load section.

Figure 16:
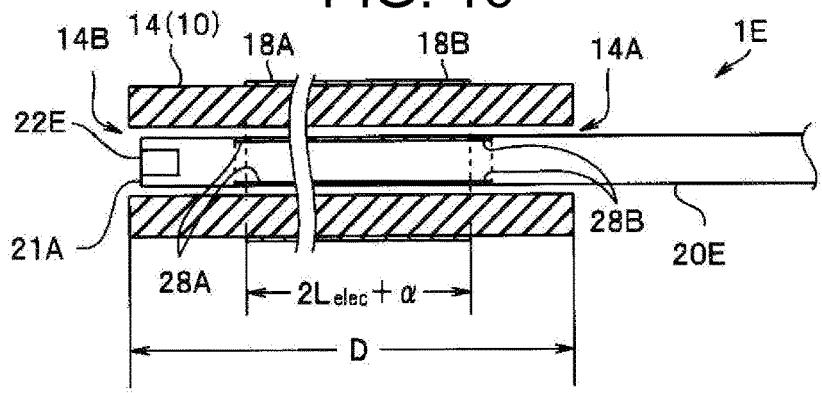
FIG. 16 is a schematic sectional view of power transmission/reception units in an endoscope system as a variation 5 of the first embodiment.

Further, as illustrated in FIG. 16, an auxiliary light probe 20E with an LED element 22E arranged in a distal end portion thereof in an endoscope system 1E is also used in a state where the distal end portion 21A does not protrude from the distal opening 14B. The received power is output to the LED element 22E as a load section. In the endoscope system 1E, the sum of the total electrode length Lelec, i.e. the total length of overlapping portions between the power transmission electrode 18 and the reception electrode 28, and a total gap α existing depending on the electrode structure is not less than 50 cm and not more than 100 cm, which is drawn to be almost the same as the length D of the channel 14.

As illustrated in FIG. 16, even in the case of the auxiliary light probe 20E whose distal end portion 21A does not protrude from the distal opening 14B, the power reception unit 29 is arranged in a position capable of receiving the alternating electric field generated by the power transmission unit 19 most efficiently in a state of being inserted into the channel 14 up to the operating position, i.e., in an inserted state where the supply of power is required.

When the auxiliary light probe 20E is used, for example, even an endoscope having no special light observation function can irradiate, if needed, an affected area with special light of a wavelength appropriate to the affected area and generated by the auxiliary light probe 20E to make more effective observations.

In an endoscope system comprising multiple treatment tools different in required power, since the output of the power source 30 needs to be adjusted according to the load of each of the treatment tools, the operation is complicated. Therefore, it is preferred that the endoscope system should have treatment tools each with power reception efficiency corresponding to the load.

For example, the counter electrode area is set small for a treatment tool for which a power of 1 W is required so that the power reception efficiency of the treatment tool will be 1/100 of the power reception efficiency of a treatment tool for which a power of 100 W is required. Alternatively, in a treatment tool that requires lower power, the resonant frequency of the power reception unit may be set to deviate from the frequency of the alternating electric field intentionally to reduce the power reception efficiency.

In other words, in an endoscope system comprising multiple treatment tools, a treatment tool with lower power required for the treatment is so set that the power transmission efficiency between the power transmission unit 19 and the power reception unit 29 will be reduced.

Since an endoscope system comprising multiple treatment tools, each comprising a power reception unit the power reception efficiency of which is set according to each load, does not need to adjust the output of the power source 30 according to the treatment tool 20, the operability is good.

<Variation 6> Power Conversion

In the endoscope system 1 and the like, high-frequency AC power received by the power reception unit 29 is used directly for a treatment through the treatment unit 22. In other words, the power used for the treatment is the same as the high-frequency power output from the power source 30, for example, a sinusoidal AC power of 13.56 MHz.

Figure 17:
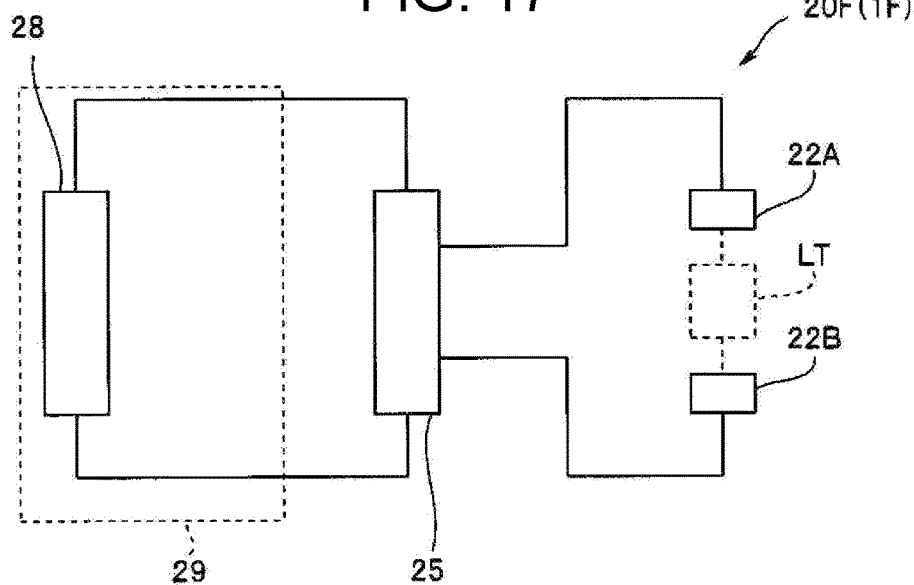
FIG. 17 is an equivalent circuit diagram of a power reception unit in an endoscope system as a variation 6 of the first embodiment.

On the other hand, as illustrated in FIG. 17, a treatment tool 20F in an endoscope system 1F as a variation 6 comprises a power conversion unit 25 for converting high-frequency power received by the power reception unit 29 and outputting the covered power to the treatment unit 22. The power conversion unit 25 converts the power, received by the power reception unit 29, to power appropriate for a treatment through the treatment unit 22. Further, though not illustrated, the treatment tool 20F in the endoscope system 1F may also comprise an output switching unit as a switch for switching between outputting the high-frequency power, received by the power reception unit 29, directly to the treatment unit 22, and outputting the high-frequency power to the power conversion unit 25.

For example, the power conversion unit 25 boosts the voltage of sinusoidal, high-frequency AC power, modulates the amplitude to obtain DC power, pulse waveform power, attenuation waveform power, square-wave power, or the like, or modulates the frequency.

As described above, the treatment tool 20F in the endoscope system 1F comprises the power conversion unit 25 for converting the waveform or the like of the power received by the power reception unit 29 into a waveform or the like of power to be applied by the treatment unit. Further, the treatment tool 20F comprises the output switching unit for applying, to the treatment unit 22, either the power received by the power reception unit 29 directly or power converted by the power conversion unit 25.

The endoscope system 1F for converting the power, received by the power reception unit 29, into power appropriate for a treatment and outputting the converted power to the treatment unit 22 can do a better treatment.

Second Embodiment

Next, an endoscope system 1G of a second embodiment will be described. Since the endoscope system 1G is similar to the endoscope systems 1 to 1F already described, the same reference numerals are given to components having the same functions to omit the description thereof.

Figure 18:
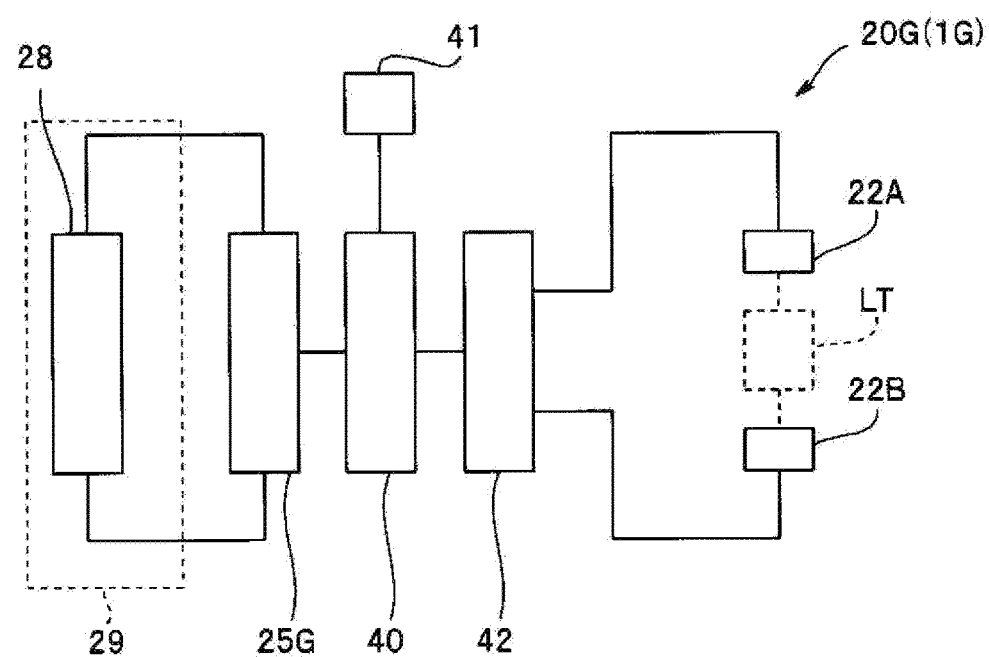
FIG. 18 is an equivalent circuit diagram of a power reception unit in an endoscope system of a second embodiment.

As illustrated in FIG. 18, a treatment tool 20G in the endoscope system 1G comprises a power conversion unit 25G for converting received AC power to DC power, a power storage unit 40 for storing power output from the power conversion unit 25G, a notice unit 41 for giving notice of a power storage state of the power storage unit 40, and a drive unit 42 for converting the DC power stored in and output from the power storage unit 40 into power according to the specification of the treatment unit 22.

The power storage unit 40 is not limited to a battery such as a lithium-ion secondary battery. For example, an electric double layer capacitor can be used particularly preferably as the power storage unit 40 because it can be charged and discharged rapidly with little degradation of capacity caused by charging and discharging, though the power storable capacity is smaller than the secondary battery. Further, the power storage unit 40 may be composed of the secondary battery and the electric double layer capacitor.

The notice unit 41 is an indication unit made up, for example, of an LED to indicate the amount of power storage (remaining power level) of the power storage unit 40. For example, the indication unit glows green when the amount of power storage is enough to allow a prolonged treatment, glows yellow when the amount of power storage is a bit small, and glows red when the amount of power storage is too small to do the treatment. Further, when the power storage unit 40 electrically discharged for the treatment stores the received power and the amount of power storage becomes enough for a treatment, the notice unit 41 may generate sound, light, vibration, or the like to notify the operator of that effect.

The endoscope system 1G has the effects of the endoscope system 1 and the like, and further can do a treatment in a state where the power reception unit 29 cannot receive power. Although an endoscope system comprising a primary battery can obtain the above effect, it is more preferred to comprise the power storage unit 40 without a need to exchange batteries.

The time required for the treatment unit 22 to use power is short and intermittent. Therefore, even if the power reception unit 29 can receive only low power, the treatment tool 20G can charge the power storage unit 40 during an interval between treatments.

Further, in a treatment tool using received power directly for a treatment, when the amount of power required for the treatment is large, there is a need to increase the strength of an electric field generated by the power transmission unit 19. However, there is a limit on the electric field strength capable of being generated by the power transmission unit 19, that is, on the power capable of being supplied to the treatment unit 22.

Since the treatment tool 20G uses, for a treatment, power stored in the power storage unit 40, there is no problem if the power required by the treatment unit 22 exceeds the power received by the power reception unit 29, and a high-power treatment can be done despite the generation of a strong electric field being unnecessary. In other words, the power transmission unit 19 does not need to generate a strong electric field even when high power is required instantaneously. Therefore, there is no danger to cause adverse effects of a leakage electric field on peripheral devices.

In other words, since the high-frequency power output from the power source 30 can be reduced in the endoscope system 1G, the electric field leakage from the power transmission unit 19 is reduced, and it is less likely to cause the heat generation problem or the like.

Of course, when power required for a treatment is low, the power received by the power reception unit 29 may be used directly for the treatment even in the endoscope system 1G.

Here, endoscope systems obtained by combining the aforementioned embodiments and variations have a combination of the effects of respective endoscope systems.

For example, an endoscope system of one embodiment comprises: a flexible endoscope comprising a flexible insertion section comprising a distal end portion in which an imaging unit is arranged, an operation section arranged on a base end side of the insertion section, and a flexible channel that passes through the insertion section; a power supply for outputting high-frequency power; and a treatment tool with a treatment unit comprising a pair of blades for supplying power to an area to be treated, the treatment unit being inserted from an insertion opening of the operation section, passing through the channel, and protruding from an opening of the distal end portion, wherein the flexible endoscope comprises a power transmission unit comprising a first transmission electrode and a second transmission electrode laid along the outer circumferential surface of the channel to generate an alternating electric field by the high-frequency current input from the power supply, and the treatment tool comprises the treatment unit for doing a treatment with power, a power reception unit comprising a first reception electrode arranged opposite to the first transmission electrode in a concentric fashion to form a first capacitor and a second reception electrode arranged opposite to the second transmission electrode in a concentric fashion to form a second capacitor identical in length to the first capacitor in a state where the treatment unit is inserted into the channel up to an operating position to receive the alternating electric field so as to form, together with the power transmission unit, a resonance circuit comprising a resonant frequency identical to the frequency of the high-frequency power input from the power source, a power storage unit for storing power received by the power reception unit and outputting, to the treatment unit, power higher than the power received by the power reception unit, and a notice unit for giving notice of a power storage state of the power storage unit.

The present invention is not limited to the aforementioned embodiments and the like, and various changes, alterations, combinations, and the like are possible without departing from the spirit of the present invention.

The invention claimed is:
1. An endoscope system comprising:
an endoscope comprising:
  an endoscope insertion section comprising a portion that is flexible, wherein the endoscope defines a channel having a distal opening in the endoscope insertion section;
  a first transmission electrode arranged to the channel, wherein the first transmission electrode is electrically connected to a power source configured to output a high-frequency power; and
  a second transmission electrode arranged to the channel, wherein the second transmission electrode is electrically connected to the power source; and
a treatment tool comprising:
  a treatment tool insertion section configured to be movably inserted in the channel of the endoscope;
  a first reception electrode arranged to the treatment tool insertion section, wherein the first reception electrode is spaced apart from the first transmission electrode to form a first capacitor;
  a second reception electrode arranged to the treatment tool insertion section, wherein the second reception electrode is spaced apart from the second transmission electrode to form a second capacitor; and
  an electrically powered treatment device attached to the treatment tool insertion section to be moved by the treatment tool insertion section, wherein the electrically powered treatment device is electrically connected to the first reception electrode and the second reception electrode to be powered to perform a treatment on a subject,
wherein the endoscope further comprises:
  a variable inductor, wherein the variable inductor, the first capacitor, and the second capacitor are electrically connected to form a resonant circuit; and
  a controller configured to control the variable inductor to adjust a resonant frequency to coincide with a frequency of the high-frequency power.

2. The endoscope system according to claim 1,
wherein in an operating position of the treatment tool, the treatment tool insertion section is configured to be arranged relative to the channel of the endoscope such that:
  the first reception electrode is spaced apart from the first transmission electrode to form the first capacitor; and
  the second reception electrode is spaced apart from the second transmission electrode to form the second capacitor.

3. The endoscope system according to claim 2,
wherein the first transmission electrode, the second transmission electrode, the first reception electrode, and the second reception electrode are arranged along a circumference of the channel.

4. The endoscope system according to claim 1,
wherein in an operating position of the treatment tool:
  the first transmission electrode and the first reception electrode are arranged in a concentric fashion to form the first capacitor; and
  the second transmission electrode and the second reception electrode are arranged in a concentric fashion to form the second capacitor.

5. The endoscope system according to claim 1,
wherein the first reception electrode and the second reception electrode are formed from a spiral coil.

6. The endoscope system according to claim 1,
wherein the electrically powered treatment device comprises a pair of blades configured to supply power to an area to be treated.

7. An endoscope system comprising:
an endoscope comprising:
  an endoscope insertion section comprising a portion that is flexible, wherein the endoscope defines a channel having a distal opening in the endoscope insertion section;
  a first transmission electrode arranged to the channel, wherein the first transmission electrode is electrically connected to a power source configured to output a high-frequency power; and
  a second transmission electrode arranged to the channel, wherein the second transmission electrode is electrically connected to the power source; and
a treatment tool comprising:
  a treatment tool insertion section configured to be movably inserted in the channel of the endoscope;
  a first reception electrode arranged to the treatment tool insertion section, wherein the first reception electrode is spaced apart from the first transmission electrode to form a first capacitor;
  a second reception electrode arranged to the treatment tool insertion section, wherein the second reception electrode is spaced apart from the second transmission electrode to form a second capacitor;
  an electrically powered treatment device attached to the treatment tool insertion section to be moved by the treatment tool insertion section, wherein the electrically powered treatment device is electrically connected to the first reception electrode and the second reception electrode to be powered to perform a treatment on a subject; and
  a power converter configured to convert a first form of a power received by the first reception electrode and the second reception electrode into a second form used by the electrically powered treatment device to perform the treatment on the subject.

8. The endoscope system according to claim 7, wherein in an operating position of the treatment tool, the treatment tool insertion section is configured to be arranged relative to the channel of the endoscope such that:
the first reception electrode is spaced apart from the first transmission electrode to form the first capacitor; and
the second reception electrode is spaced apart from the second transmission electrode to form the second capacitor.

9. The endoscope system according to claim 8, wherein the first transmission electrode, the second transmission electrode, the first reception electrode, and the second reception electrode are arranged along a circumference of the channel.

10. The endoscope system according to claim 7, wherein in an operating position of the treatment tool:
the first transmission electrode and the first reception electrode are arranged in a concentric fashion to form the first capacitor; and
the second transmission electrode and the second reception electrode are arranged in a concentric fashion to form the second capacitor.

11. The endoscope system according to claim 7, wherein the first reception electrode and the second reception electrode are formed from a spiral coil.

12. The endoscope system according to claim 7, wherein the electrically powered treatment device comprises a pair of blades configured to supply power to an area to be treated.

13. An endoscope system comprising:
an endoscope comprising:
an endoscope insertion section comprising a portion that is flexible, wherein the endoscope defines a channel having a distal opening in the endoscope insertion section;
a first transmission electrode arranged to the channel, wherein the first transmission electrode is electrically connected to a power source configured to output a high-frequency power; and
a second transmission electrode arranged to the channel, wherein the second transmission electrode is electrically connected to the power source; and
a treatment tool comprising:
a treatment tool insertion section configured to be movably inserted in the channel of the endoscope;
a first reception electrode arranged to the treatment tool insertion section, wherein the first reception electrode is spaced apart from the first transmission electrode to form a first capacitor;
a second reception electrode arranged to the treatment tool insertion section, wherein the second reception electrode is spaced apart from the second transmission electrode to form a second capacitor;
an electrically powered treatment device attached to the treatment tool insertion section to be moved by the treatment tool insertion section, wherein the electrically powered treatment device is electrically connected to the first reception electrode and the second reception electrode to be powered to perform a treatment on a subject; and
a power storage device configured to store the power received by the first reception electrode and the second reception electrode, and to output the stored power to the electrically powered treatment device.

14. The endoscope system according to claim 13, wherein in an operating position of the treatment tool, the treatment tool insertion section is configured to be arranged relative to the channel of the endoscope such that:
the first reception electrode is spaced apart from the first transmission electrode to form the first capacitor; and
the second reception electrode is spaced apart from the second transmission electrode to form the second capacitor.

15. The endoscope system according to claim 14, wherein the first transmission electrode, the second transmission electrode, the first reception electrode, and the second reception electrode are arranged along a circumference of the channel.

16. The endoscope system according to claim 13, wherein in an operating position of the treatment tool:
the first transmission electrode and the first reception electrode are arranged in a concentric fashion to form the first capacitor; and
the second transmission electrode and the second reception electrode are arranged in a concentric fashion to form the second capacitor.

17. The endoscope system according to claim 13, wherein the first reception electrode and the second reception electrode are formed from a spiral coil.

18. The endoscope system according to claim 13, wherein the electrically powered treatment device comprises a pair of blades configured to supply power to an area to be treated.

19. The endoscope system according to claim 13, wherein the treatment tool further comprises a display configured to display a power storage state of the power storage device.

20. The endoscope system according to claim 13, wherein the power storage device is configured such that the power output is higher than the power received.

* * * * *